(12) United States Patent
Riobo Aboy

(10) Patent No.: US 8,926,521 B2
(45) Date of Patent: *Jan. 6, 2015

(54) METHOD FOR BLOOD PRESSURE MEASUREMENT FROM NONINVASIVE OSCILLOMETRIC PRESSURE SIGNALS

(75) Inventor: Pedro Mateo Riobo Aboy, Portland, OR (US)

(73) Assignee: Mortara Instrument, Inc., Milwaukee, WI (US)

( * ) Notice: Subject to any disclaimer, the term of this patent is extended or adjusted under 35 U.S.C. 154(b) by 839 days.

This patent is subject to a terminal disclaimer.

(21) Appl. No.: 13/047,780

(22) Filed: Mar. 14, 2011

(65) Prior Publication Data

US 2011/0166460 A1     Jul. 7, 2011

Related U.S. Application Data

(63) Continuation of application No. 12/052,659, filed on Mar. 20, 2008, now Pat. No. 7,927,283.

(60) Provisional application No. 60/895,902, filed on Mar. 20, 2007.

(51) Int. Cl.
  *A61B 5/02* (2006.01)
  *A61B 5/0225* (2006.01)
  *A61B 5/022* (2006.01)

(52) U.S. Cl.
  CPC ........... *A61B 5/0225* (2013.01); *A61B 5/02225* (2013.01)
  USPC .......................................... 600/490; 600/500

(58) Field of Classification Search
  USPC .................. 600/485, 490, 493–496
  See application file for complete search history.

(56) References Cited

U.S. PATENT DOCUMENTS

| | | | | |
|---|---|---|---|---|
| 5,042,496 A * | 8/1991 | Sjonell | .......................... | 600/490 |
| 2006/0195035 A1 * | 8/2006 | Sun | ............................. | 600/503 |
| 2006/0253040 A1 * | 11/2006 | Stergiopoulos et al. | ...... | 600/493 |
| 2007/0118036 A1 * | 5/2007 | Hersh et al. | .................... | 600/485 |

OTHER PUBLICATIONS

A Novel Algorithm to Estimate the Pulse Pressure Variation Index, Mateo Aboy et al, IEEE Transactions on Niomedical Engineering, vol. 51, No. 12, Dec. 2004.*

* cited by examiner

*Primary Examiner* — Michael D'Angelo
(74) *Attorney, Agent, or Firm* — Mateo Aboy; Aboy & Associates PC

(57) ABSTRACT

Disclosed embodiments include a method for measuring noninvasive blood pressure from an oscillometric signal and a cuff pressure signal implemented in a medical apparatus comprising: (a) calculating a pulse pressure signal by subtracting an upper and a lower envelope of the oscillometric signal; and (b) calculating without the use of beat detection a mean arterial pressure, a systolic blood pressure, and a diastolic blood pressure from said oscillometric signal, said cuff pressure signal, and a plurality of thresholds a device with at least one processor.

4 Claims, 10 Drawing Sheets

_US 8,926,521 B2_

METHOD FOR BLOOD PRESSURE MEASUREMENT FROM NONINVASIVE OSCILLOMETRIC PRESSURE SIGNALS

CROSS-REFERENCE TO RELATED APPLICATIONS

This application is a Continuation of U.S. patent application Ser. No. 12/052,659 filed on Mar. 20, 2008, which claims the benefit of U.S. Provisional Application No. 60/895,902 filed on Mar. 20, 2007, and are hereby incorporated by reference in their entirety.

TECHNICAL FIELD

Disclosed embodiments related to blood pressure monitoring. Specifically, they related to automatic oscillometric non-invasive blood pressure measurement methods and apparatuses.

BACKGROUND

Various techniques have been proposed for noninvasive measurement of blood pressure. A technique employed by many commercial monitoring systems is based on the well-known "oscillometric" method. The oscillometric technique requires measuring the pulsations induced by the artery as the cuff is inflated and deflated. As the cuff inflates to a predetermined pressure above the systolic blood pressure, the artery of the arm is compressed and the passage of the blood is stopped. At this point no oscillometric pulsation is sensed by the device. Then, the cuff is gradually deflated and the oscillations become increasingly significant until the pulse pressure in these oscillations reaches a maximum amplitude. The point at which the oscillations have a maximum amplitude corresponds to the mean arterial pressure (MAP) on the cuff pressure signal. Systolic blood pressure (SBP) and diastolic blood pressure (DBP) are then calculated empirically based on the MAP as two different percentage points before and after the MAP point. Numerous blood pressure measurement-related inventions have been proposed based on the underlying principle of the oscillometric technique such as U.S. Pat. Nos. 4,984,577, 7,300,404, 7,153,269, 7,041,060, 7,052,465, 7,118,535, and 7,311,669. Related-art references of the oscillometric technique typically rely on performing some type of beat detection in order to calculate the pulse pressure in the oscillometric signal and determine the heart rate, and rely on two fixed MAP-based thresholds to determine SBP and DBP. Improved methods can be obtained by eliminating the need for automatic detection algorithms. Additionally, improvements on the basic oscillometric method can be made in order to increase the robustness to motion artifact.

BRIEF DESCRIPTION OF THE DRAWINGS

Disclosed embodiments are illustrated by way of example, and not by way of limitation, in the figures of the accompanying drawings.

DETAILED DESCRIPTION

Disclosed embodiments include a method for measuring non-invasive blood pressure from an oscillometric signal and a cuff pressure signal implemented in a medical apparatus comprising: (a) calculating a pulse pressure signal by subtracting an upper and a lower envelope of the oscillometric signal; and (b) calculating a mean arterial pressure, a systolic blood pressure, and a diastolic blood pressure from the oscillometric signal, the cuff pressure signal, and a plurality of thresholds using a device with at least one processor. In a particular embodiment, and without limitation, the upper and lower envelopes are calculated based on rank-order filters applied to the oscillometric signal. In another embodiment, the oscillometric signal is filtered with one or more frequency selective filters prior to the application of the rank-order filters, and the pulse pressure signal is further filtered using a median filter and a lowpass filter to eliminate artifacts. Calculating the mean arterial pressure is based on identifying an index value corresponding to a global maximum value in the pulse pressure signal and evaluating the cuff pressure signal at said index value. In one embodiment, the step of calculating the systolic blood pressure and the diastolic blood pressure is based on evaluating the cuff pressure signal at index values corresponding to specific percent values of the maximum value in the pulse pressure signal, and said percent values specified by the thresholds. In some embodiments, the plurality of thresholds are a function of the mean arterial pressure, resulting in a vector threshold with multiple scalar thresholds each corresponding to a different mean arterial pressure. In other embodiments, the plurality of thresholds may also be a function of an arm circumference, resulting in a vector threshold with multiple scalar thresholds each corresponding to a different arm circumference. In yet another embodiments, the plurality of thresholds are a function of a heart rate, resulting in a vector threshold with multiple scalar thresholds each corresponding to a different heart rate.

Figure 1:
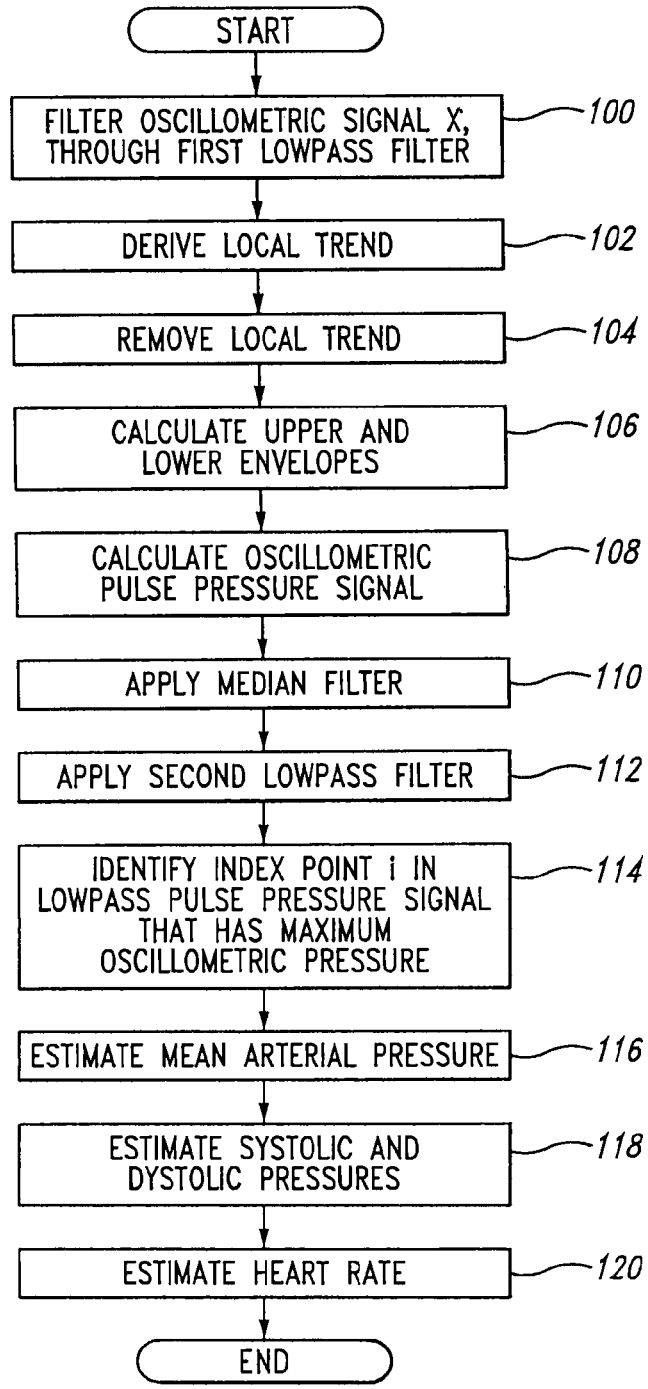
FIG. 1 shows a block diagram of an embodiment of a method for a non-invasive measurement of blood pressure.

FIG. 1 shows a block diagram of a method, according to a particular embodiment and without limitation, for a non-invasive measurement of blood pressure. The method uses as input a oscillometric signal $x_1(n)$ and a cuff pressure signal $x_2(n)$. This method is accomplished by filtering the oscillometric signal $x_1(n)$ using linear filters to remove artifacts, calculating the pulse pressure envelope without beat detection by using rank-order filters, and determining the heart rate based on a spectrum analysis of the oscillometric signal $x_1(n)$, as follows:

Step 100—Lowpass filter the input oscillometric signal $x_1(n)$ to remove high frequency noise and artifact $$x_1^l(n) = x_1(n) * h_l(n) = \sum_{k=0}^{M_l} h_l(n) x_1(n-k) \qquad (1)$$

where $M_l$ denotes the filter-order, n the sample index, and $h_l(n)$ the impulse response of the lowpass filter.

Step 102—Estimate the local trend of the lowpass filtered oscillometric signal using a linear filter $$x_1^t(n) = x_1^l(n) * h_t(n) = \sum_{k=0}^{M_t} h_t(n) x_1^l(n-k) \qquad (2)$$

where $M_t$ and $h_t(n)$ are defined depending for different patients populations and conditions. $M_t$ denotes the filter-order, n the sample index, and $h_t(n)$ the impulse response of the lowpass filter used to estimate the trend of the filtered oscillometric signal $x_1^l(n)$. The filter order and the impulse response for the previous filters are determined based on a selected patient population under a particular set of environmental conditions.

Step 104—Remove local trend from the filtered oscillometric signal $$x_1^h(n) = x_1^l(n) - x_1^t(n) = \sum_{k=0}^{M_l} h_l(n) x_1(n-k) - \sum_{k=0}^{M_t} h_t(n) x_1^l(n-k) \qquad (3)$$

where $x_1^h(n)$ denotes the de-trended lowpass filtered signal used for further processing.

Step 106—Estimate the upper and lower envelopes of the detrended and lowpass filtered oscillometric signal $x_1^h(n)$ using a rank-order filter $$(u(n), l(n)) = \Pi\{x_1^h(n), w_l, u_p, l_p\} \qquad (4)$$

where u(n) and l(n) denote the upper and lower envelopes, respectively, $w_l$ is the window length (i.e. number of samples use to calculate the percentiles), $u_p$ represents the upper percentile, and $l_p$ represents the lower percentiles (configurable).

Step 108—Calculate the oscillometric pulse pressure, $p_p(n)$ by subtracting the lower envelope from the upper envelope signal $$p_p(n) = u(n) - l(n) \qquad (5)$$

In some embodiments, steps 106 and 108 are combined to save memory. That is, the intermediate results of step 106 are not stored in memory, but used immediately in step 108 to calculate the oscillometric pulse pressure signal ?which is subsequently stored in memory.

Step 110—Apply a median filter to the pulse pressure signal $p_p(n)$ to remove components due to artifact.

$$p_p^m = \Pi\{p_p(n), w_l^m\} \qquad (6)$$

where $w_l^m$ denotes the median filter window length and is defined for specific patient populations and conditions.

Step 112—Lowpass filter the pulse pressure signal $p_p^m(n)$ to remove high frequency components due to artifact, $$p_p^l(n) = p_p^m(n) * h_p(n) = \sum_{k=0}^{M_p} h_p(n) p_p^m(n-k) \qquad (7)$$

where $M_p$ and $h_p(n)$ defined for different patients populations and conditions. $M_p$ denotes the filter-order, n the sample index, and $h_p(n)$ the impulse response of the lowpass filter.

Step 114—Identify the location of the maximum oscillometric pulse pressure, $$i = \arg\max_{0 \leq n \leq L} \{p_p^l(n)\} \qquad (8)$$

Step 116—Estimate mean arterial pressure, m, by finding the cuff pressure at sample i $$m = x_2(i) \qquad (9)$$

Step 118—Estimate the systolic, s, and diastolic, d, pressures by identifying the $t_s$ and $t_d$ percent points (two vectors or matrices defined as a function of the patient population and conditions such as mean arterial pressure, arm circumference, and heart rate) preceding and following i on the $p_p^f(n)$ signal and identifying them in the cuff pressure signal $x_2(n)$.

Step 120—Estimate the heart rate $f_c$ (cardiac frequency) by finding the frequency corresponding to the maximum spectrum amplitude in the range of physiologic interest, $$f_c = \arg\max_{f_l \leq f \leq f_h} \frac{1}{N} \left| \sum_{n=-\infty}^{\infty} x_w^h(n) w_R(n) e^{-j2\pi f n} \right| \approx \qquad (10)$$
$$\arg\max_{f_l \leq f \leq f_h} |FFT\{x_w^h(n) w_R(n), N\}|$$

where by default $x_w^h(n) = x_1^h(i - \alpha f_s : i + \alpha f_s)$, that is, a $2\alpha$ second window of the detrended oscillometric signal centered around the maximum pulse pressure sample i, and N denotes the maximum N-point FFT can be computed, and $w_R(n)$ a window to reduce the sidelobes such as the Blackman window.

The description of the embodiment above does not represent a step-by-step sequence. The operations and methods detailed may be applied following a different sequence. The method can be implemented in hardware and firmware to make a blood pressure monitor and in software as part of a program to analyze oscillometric signals in order to measure blood pressure.

Estimating the oscillometric envelope without performing beat detection by using rank-order filters improves the robustness to motion artifact and makes the oscillometric technique more reliable. The threshold vectors can easily be generalized to multiple dimensions by including the dependence on the arm-circumference, heart rate, and other parameters. Since the dependence of the thresholds on the MAP, arm-circumference, and heart rate is conditioned on the hardware used to obtain the oscillometric and cuff pressure signals, the determination of these thresholds must be performed using a systematic optimization study where the performance of the method is monitored as these parameters are linearly varied.

Figure 2:
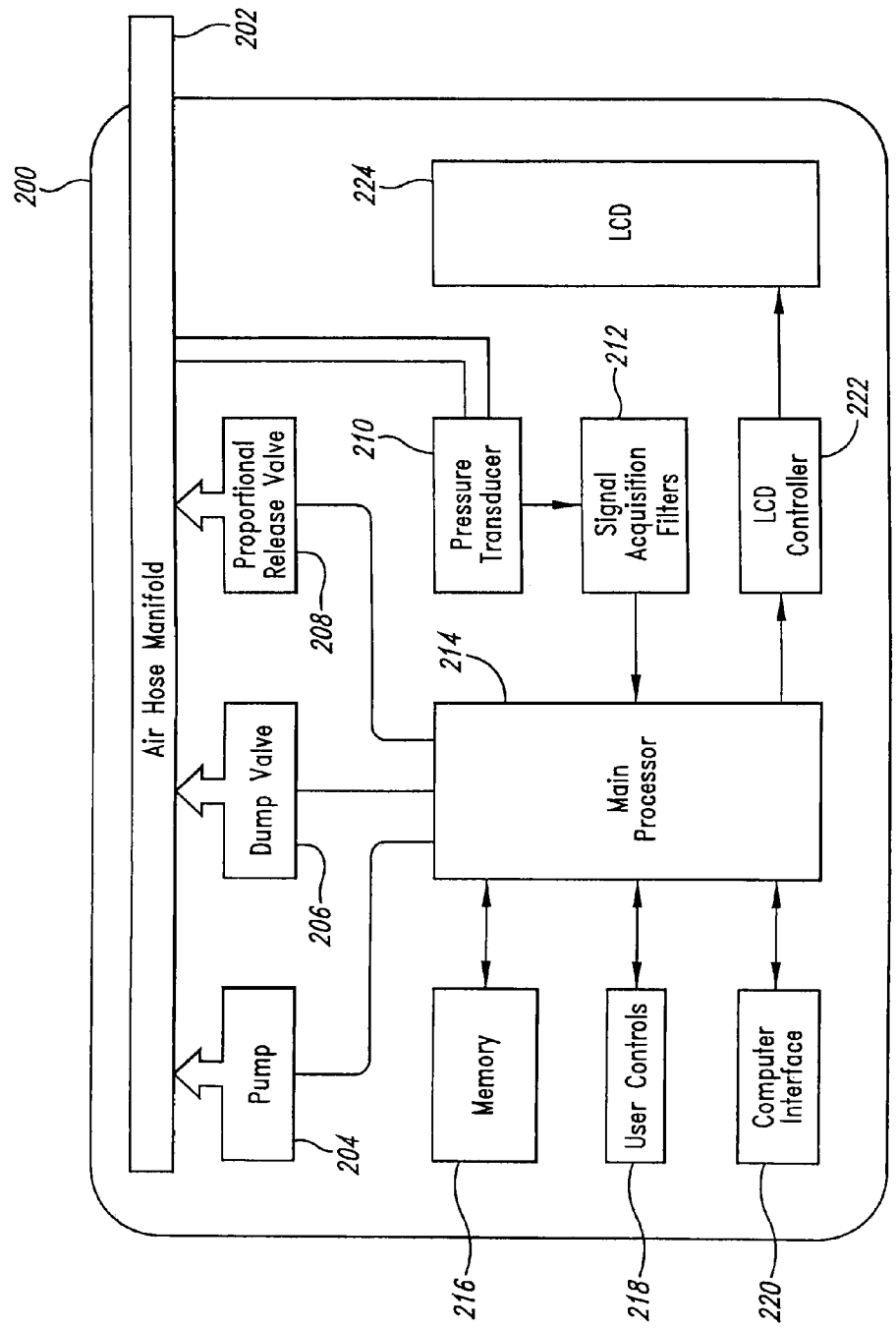
FIG. 2 shows a general block diagram of a blood pressure monitor.

FIG. 2 shows a general block diagram of a blood pressure monitor 200. The blood pressure monitor 200 has an air hose manifold 202 to connect to a pressure cuff (not shown). The blood pressure monitor 200 includes a pump 204, a dump valve 206 and a proportional release value 208, all connected to the air hose manifold 202. The pump 202 is configured to inflate the pressure cuff. The proportional release valve 208 is configured to slowly release air from the cuff.

The blood pressure monitor 200 includes a pressure transducer 210 and signal acquisition filters 212. The pressure transducer 210 is configured to measure the cuff pressure. The signal acquisition filters 220 are configured to take samples of the cuff pressure and generate oscillometric signal $x_1(n)$ and cuff pressure signal $x_2(n)$.

The blood pressure monitor 200 includes a processor 214 and a memory 216. The processor 214 is configured to process the oscillometric signal $x_1(n)$ and cuff pressure signal $x_2(n)$. The processor 214 is configured to execute instructions stored in the memory 216. In some embodiments the instructions comprise the steps describe in FIG. 1 and the discussion thereof. The memory 216 is configured to store the results of the processing. In some embodiments, the blood pressure monitor 200 includes user controls 218 and a computer interface 220. The user controls 218 are configured to accept instructions from a user and transfer the instructions to the processor 214. The computer interface 220 is configured to transfer information between the blood pressure monitor 200 to an external computing device.

In some embodiments, the patient monitor includes a graphics controller 222 and a graphics user interface 224. The graphics user interface 224 is configured to display information retrieved from the memory 216 for the user to view. The graphics controller 222 is configured to render the information retrieved from the memory 216 into a format usable by the graphics user interface 224.

In an exemplary embodiment, and without limitation, a sample rate of 50 hz is used and the rank-order filters use a window length of 251 points. The upper envelope is calculated using a 90th percentile rank-order filter, and the lower envelope with a 10th percentile. The $t_s$ vector has a length of 120 points and it linearly decreases from 0.6 to 0.5 as a function of the MAP (0.5 corresponding to a MAP of 60 mmHg and 0.9 to a MAP of 180 mmHg). Analogously, the $t_d$ vector has a length of 120 points and it linearly decreases from 0.95 to 0.6 as a function of the MAP (0.95 corresponding to a MAP of 60 mmHg and 0.6 to a MAP of 180 mmHg). Using vector thresholds as a function of the MAP significantly improves the accuracy of the oscillometric method. Estimating the oscillometric envelope without performing beat detection by using rank-order filters improves the robustness to motion artifact and makes the oscillometric technique more reliable. These threshold vectors can easily be generalized to multiple dimensions by including the dependence on the arm-circumference, heart rate, and other parameters. Since the dependence of the thresholds on the MAP, arm-circumference, and heart rate is conditioned on the hardware used to obtain the oscillometric and cuff pressure signals, the determination of these thresholds must be performed using a systematic optimization study where the performance of the method is monitored as these parameters are linearly varied.

Figure 3:
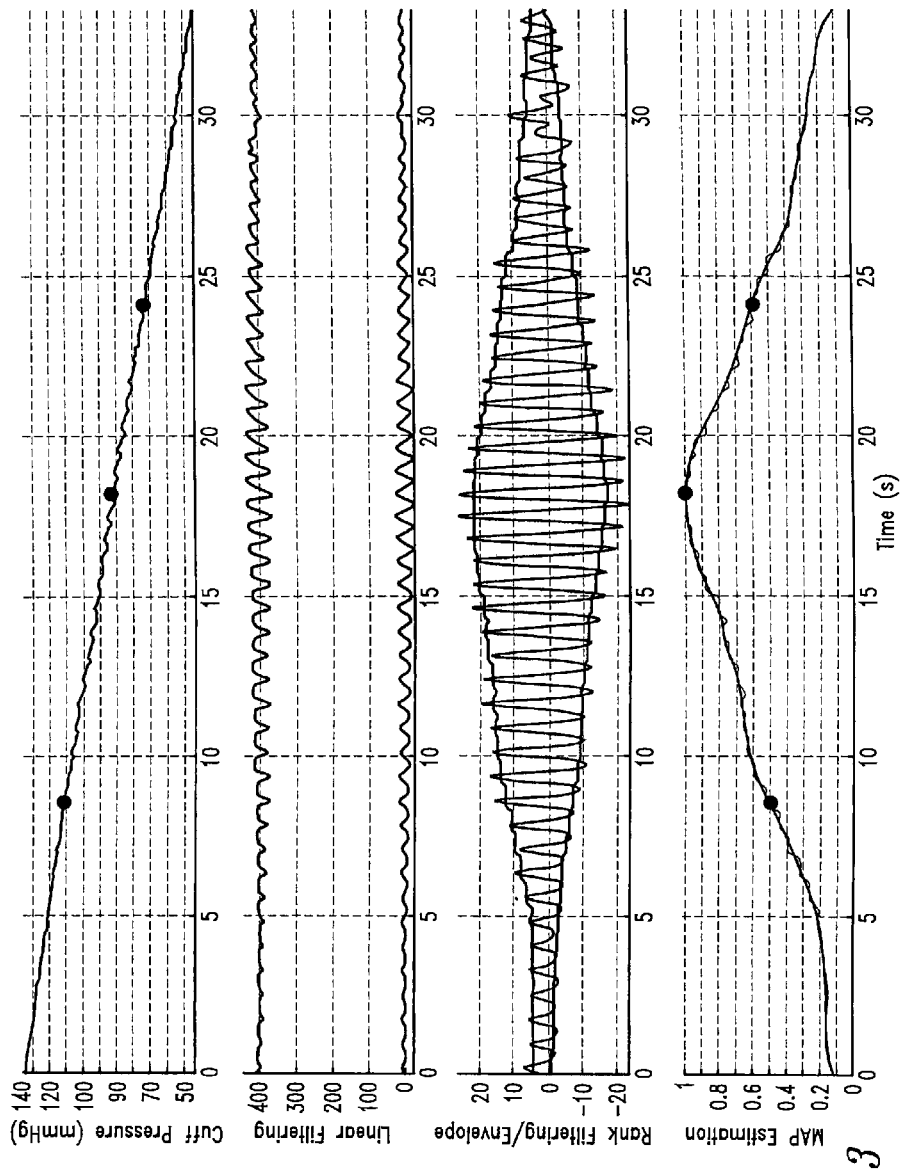
FIG. 3 illustrates the results of each method step on a normotensive patient.
Figure 4:
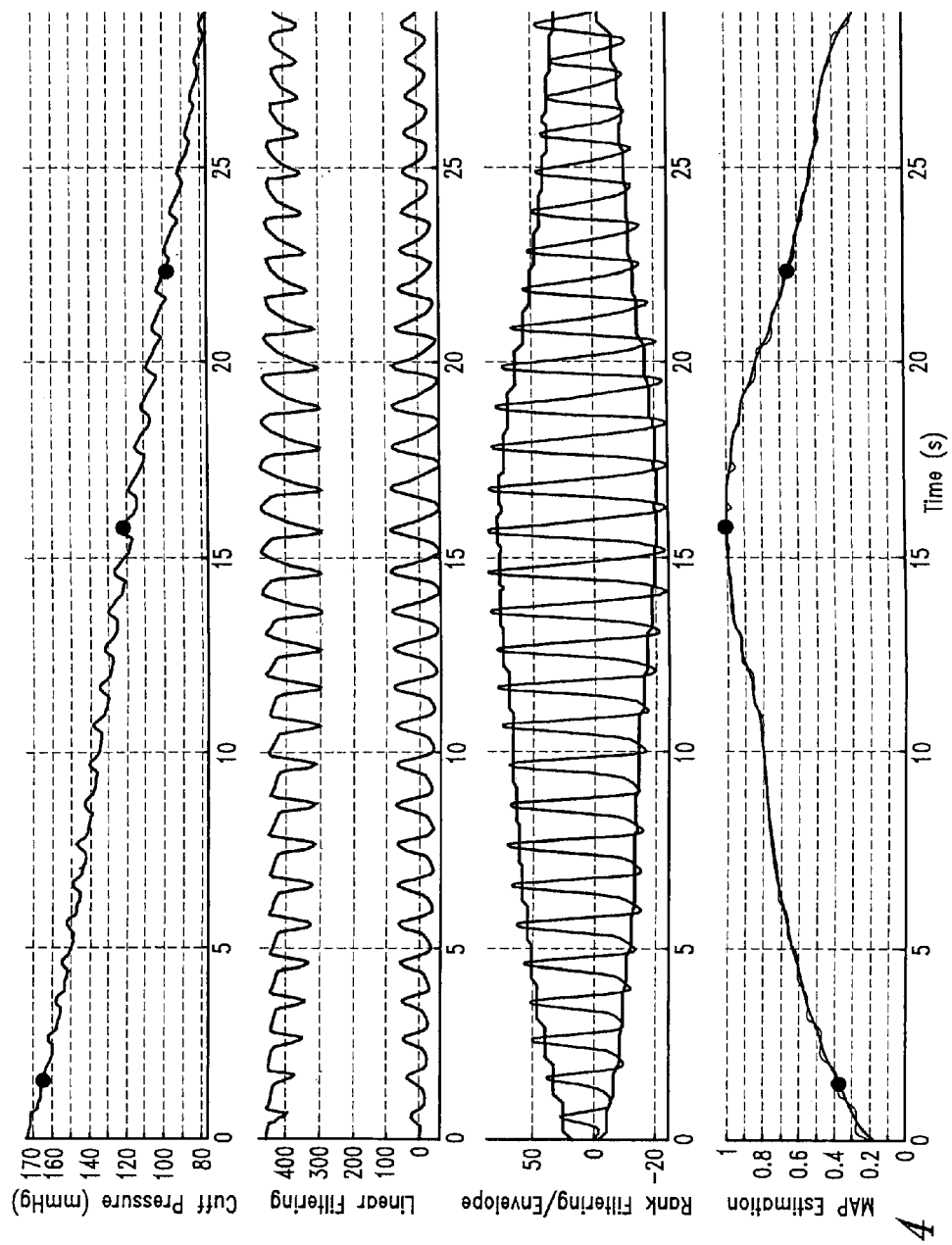
FIG. 4 illustrates the results of each method step on a hypertensive patient.
Figure 5:
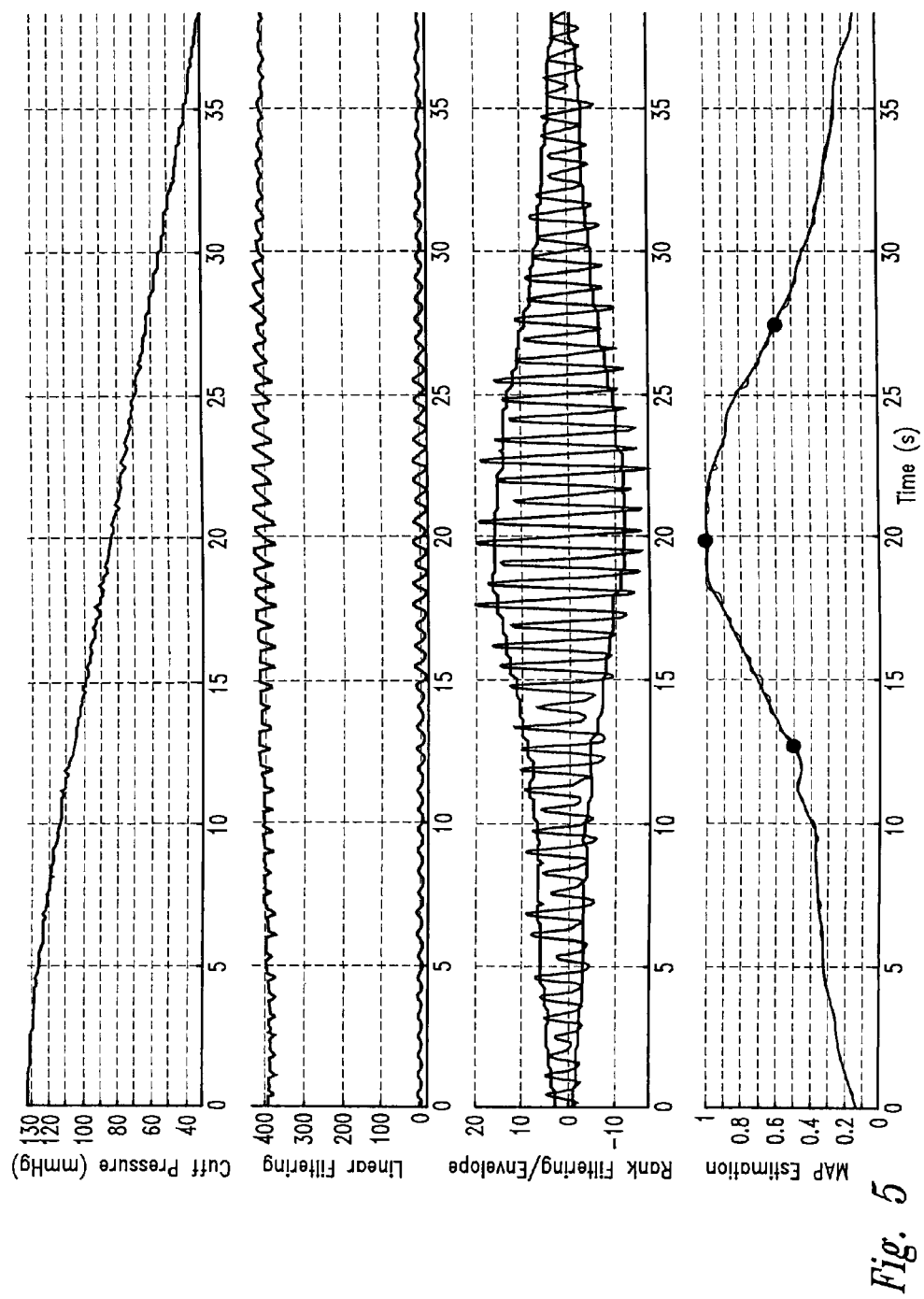
FIG. 5 illustrates the results of each method step on a hypotensive patient.
Figure 6:
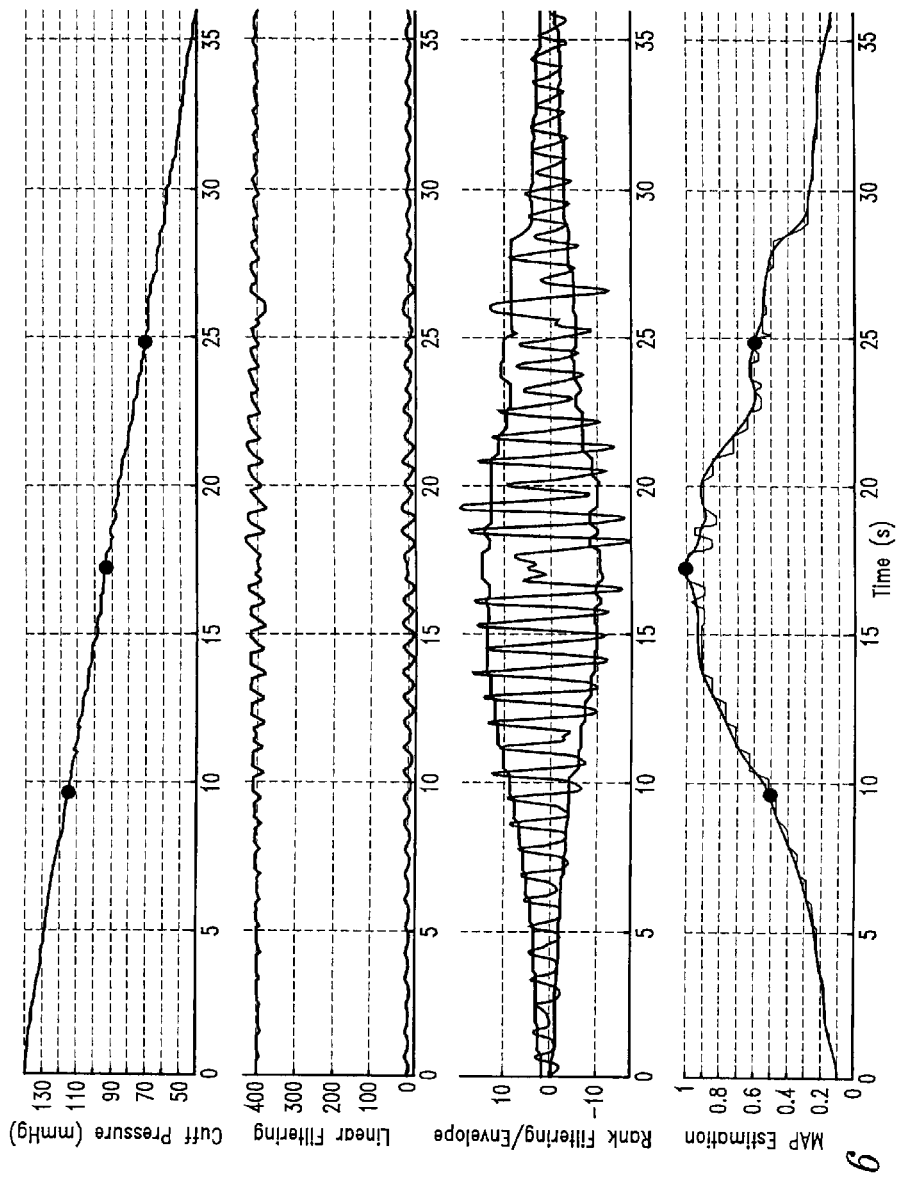
FIG. 6 illustrates the results of each method step on a patient with motion artifact.
Figure 7:
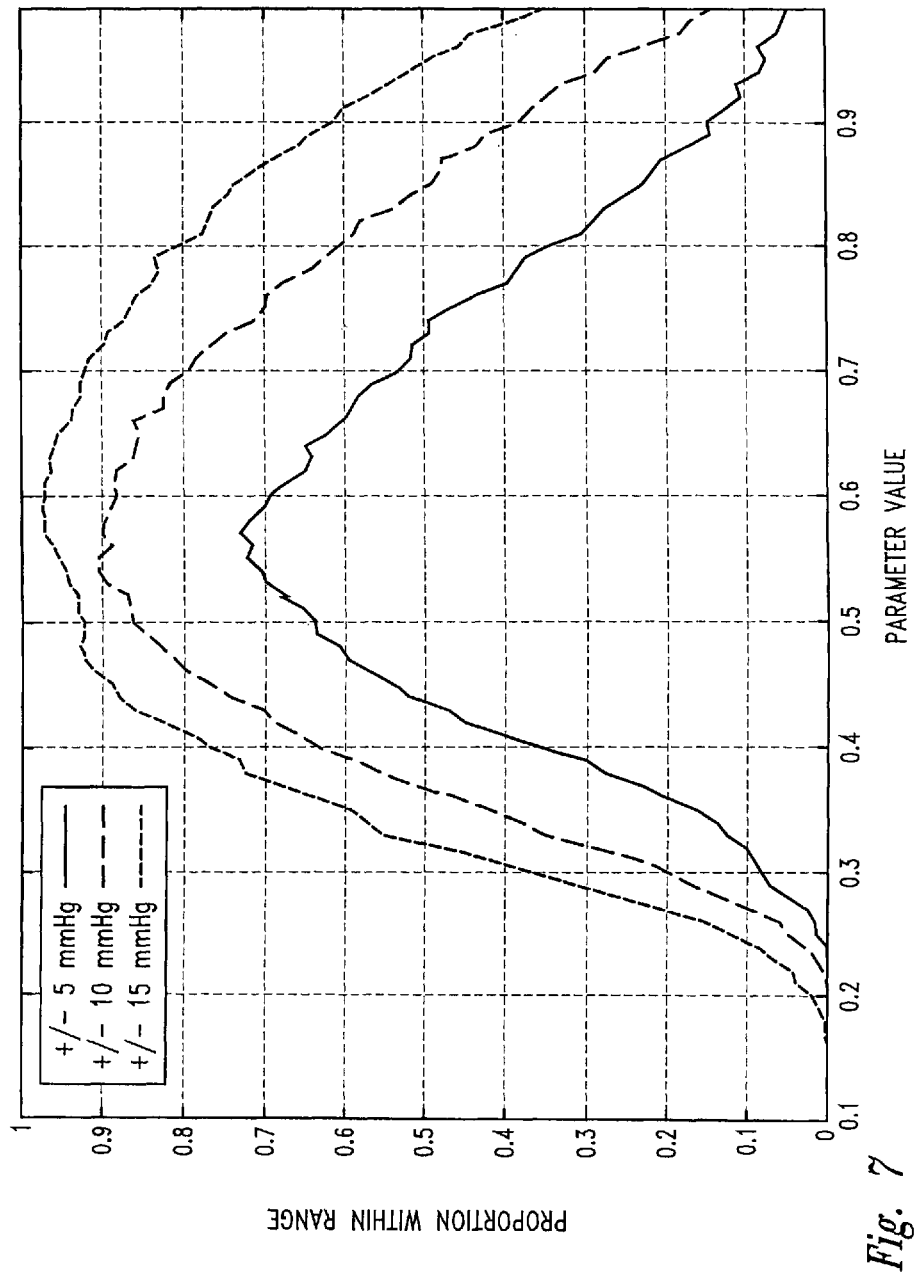
FIG. 7 shows the performance of the method as a function of the threshold value for SBP.
Figure 8:
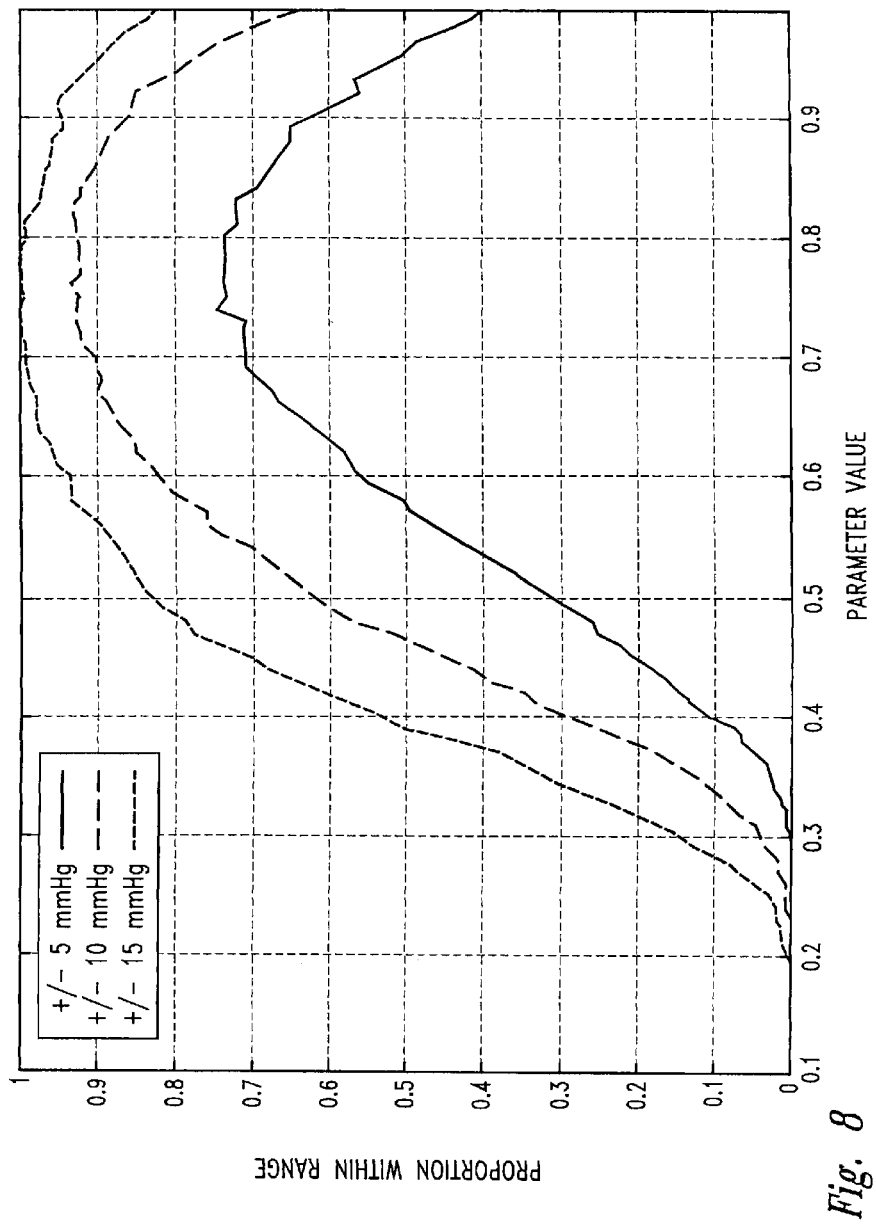
FIG. 8 shows the performance of the method as a function of the threshold value for DBP.

FIG. 3 illustrates the results of each method step on a normotensive patient. Specifically, it shows the effect of applying the lowpass and highpass filters, the estimation of the upper and lower envelopes using rank order filters, the determination of the oscillometric envelope using the difference of the upper and lower envelopes calculated using rank-order filters, the final oscillometric envelope after rank-order filtered and lowpassed filtered, and the determination of the MAP, SBP, DBP, and heart rate without beat-detection. FIG. 4 illustrates similar results for each method step on a hypertensive patient. FIG. 5 illustrates similar results for each method step on a hypotensive patient. FIG. 6 illustrates the results of each method step on a patient with motion artifact. FIG. 7 shows the performance of the method as a function of the threshold value for SBP and FIG. 8 shows the performance of the method as a function of the threshold value for DBP. These two figures also serve to illustrate the procedure to determine the single optimal threshold for SBP and DBP for a given hardware/firmware architecture. In all these plots we show the embodiment where the method is applied during linear cuff deflation. Alternative embodiments comprising the same steps are applicable to situations there noninvasive blood pressure is to be determined during cuff inflation. The method steps are the same regardless of the method of deflation (i.e. linear or step-by-step).

Figure 9:
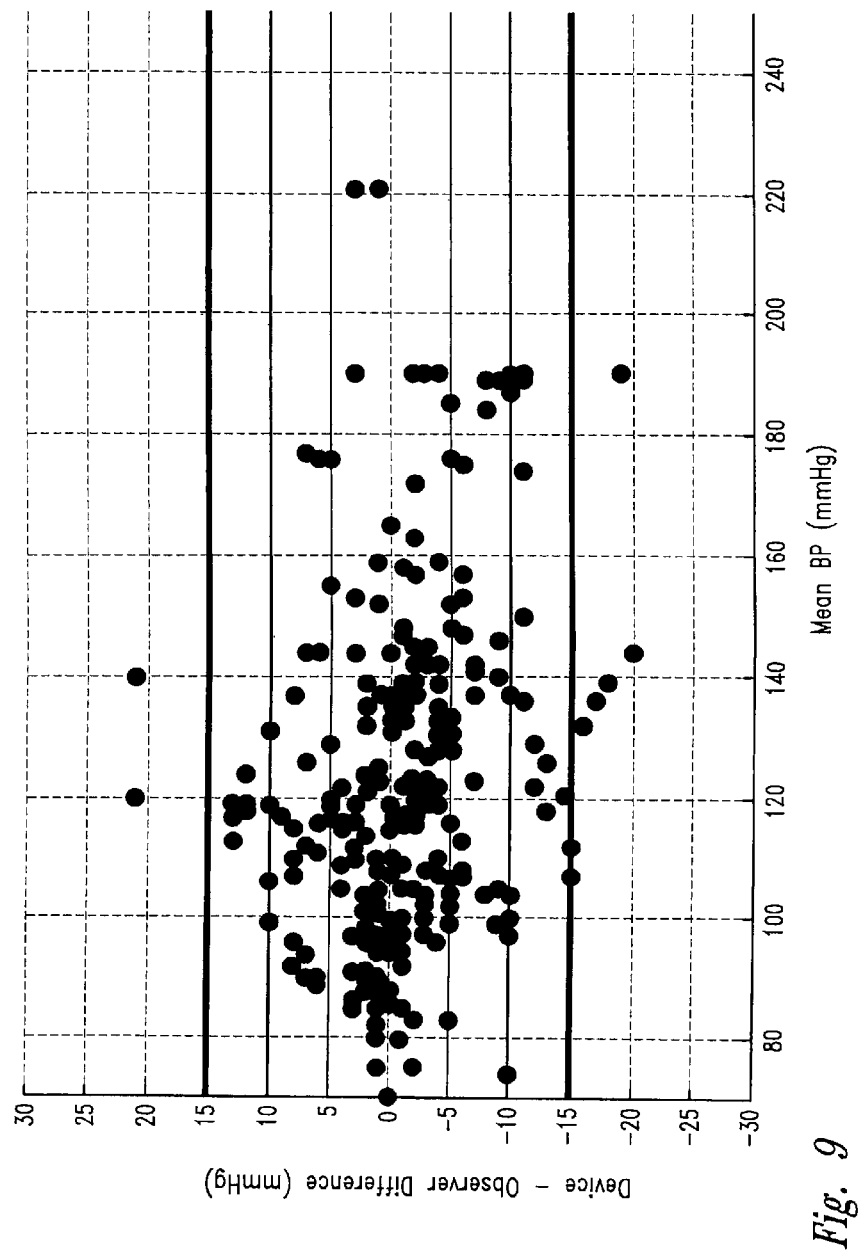
FIG. 9 shows a Bland-Altman plot illustrating the accuracy of the method for systolic blood pressure on a large patient population.
Figure 10:
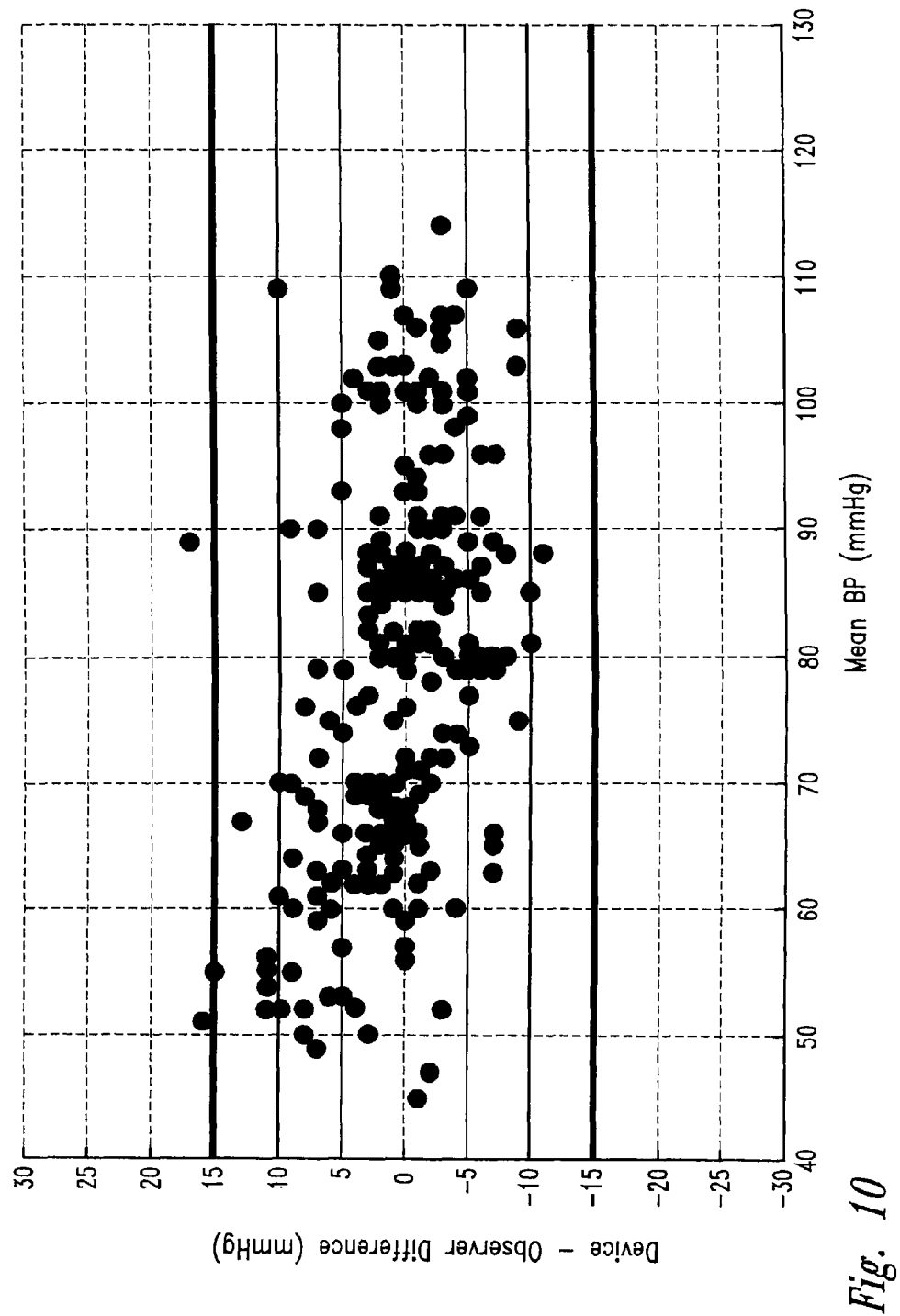
FIG. 10 shows a Bland-Altman plot illustrating the accuracy of the method for diastolic blood pressure on a large patient population.

FIG. 9 shows a Bland-Altman plot illustrating the accuracy of the method for systolic blood pressure on a large patient population and FIG. 10 shows a Bland-Altman plot illustrating the accuracy of the method for diastolic blood pressure on a large patient population. While particular embodiments have been described, it is understood that, after learning the teachings contained in this disclosure, modifications and generalizations will be apparent to those skilled in the art without departing from the spirit of the disclosed embodiments. It is noted that the foregoing embodiments and examples have been provided merely for the purpose of explanation and are in no way to be construed as limiting. While the system has been described with reference to various embodiments, it is understood that the words that have been used herein are words of description and illustration, rather than words of limitation. Further, although the system has been described herein with reference to particular means, materials and embodiments, the actual embodiments are not intended to be limited to the particulars disclosed herein; rather, the system extends to all functionally equivalent structures, methods and uses, such as are within the scope of the appended claims. Those skilled in the art, having the benefit of the teachings of this specification, may effect numerous modifications thereto and changes may be made without departing from the scope and spirit of the disclosed embodiments in its aspects.

The described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open? terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Accordingly, the invention is not limited except as by the appended claims.

What is claimed is:

1. A medical apparatus, comprising:
   (a) a non-invasive blood pressure monitor comprising a pressure transducer and a pressure cuff; and
   (b) a processor in said non-invasive blood pressure monitor configured for 1) calculating a pulse pressure signal by subtracting an upper and a lower envelope of an oscillometric signal acquired with said non-invasive blood pressure monitor, 2) calculating without employing beat detection a mean arterial pressure, a systolic blood pressure, and a diastolic blood pressure from said oscillometric signal, a cuff pressure signal obtained with said pressure cuff, and a plurality of thresholds by 1) calculating said mean arterial pressure by identifying an index value corresponding to a global maximum value in said pulse pressure signal and evaluating said cuff pressure signal at said index value, 2) calculating said systolic blood pressure and said diastolic blood pressure by evaluating said cuff pressure signal at index values corresponding to specific percent values of said maximum value in said pulse pressure signal, said percent values specified by said plurality of thresholds, and wherein said plurality of thresholds are a function of the mean arterial pressure, resulting in a vector threshold with multiple scalar thresholds each corresponding to a different mean arterial pressure, and 3) reporting an output result including said systolic blood pressure and said diastolic blood pressure calculations.

2. The medical apparatus of claim 1, wherein said plurality of thresholds are a function of an arm circumference, resulting in a vector threshold with multiple scalar thresholds each corresponding to a different arm circumference.

3. The medical apparatus of claim 1, wherein said plurality of thresholds are a function of heart rate.

4. The medical apparatus of claim 1, further comprising estimating the heart rate based on spectral analysis of said oscillometric signal.

* * * * *